United States Patent
Brown et al.

(10) Patent No.: US 10,996,332 B2
(45) Date of Patent: May 4, 2021

(54) SYSTEMS AND METHODS OF COMBINED PHASED-ARRAY AND FRESNEL ZONE PLATE BEAMFORMING EMPLOYING DELAY-CORRECTED FRESNEL SUB-APERTURES

(71) Applicant: DALHOUSIE UNIVERSITY, Halifax (CA)

(72) Inventors: Jeremy Brown, Halifax (CA); Katherine Latham, Dartmouth (CA)

(73) Assignee: DALHOUSIE UNIVERSITY, Halifax (CA)

(*) Notice: Subject to any disclaimer, the term of this patent is extended or adjusted under 35 U.S.C. 154(b) by 496 days.

(21) Appl. No.: 15/756,833

(22) PCT Filed: Feb. 25, 2016

(86) PCT No.: PCT/CA2016/050193
§ 371 (c)(1),
(2) Date: Mar. 1, 2018

(87) PCT Pub. No.: WO2017/041166
PCT Pub. Date: Mar. 16, 2017

(65) Prior Publication Data
US 2018/0246207 A1 Aug. 30, 2018

Related U.S. Application Data

(60) Provisional application No. 62/215,548, filed on Sep. 8, 2015, provisional application No. 62/237,414, filed on Oct. 5, 2015.

(51) Int. Cl.
*H04B 1/02* (2006.01)
*G01S 15/89* (2006.01)
(Continued)

(52) U.S. Cl.
CPC ............ *G01S 15/8927* (2013.01); *A61B 8/12* (2013.01); *A61B 8/4488* (2013.01);
(Continued)

(58) Field of Classification Search
None
See application file for complete search history.

(56) References Cited

U.S. PATENT DOCUMENTS

| 4,145,931 A | 3/1979 | Tancrell |
| 5,301,168 A | 4/1994 | Miller |

(Continued)

FOREIGN PATENT DOCUMENTS

WO 2008033528 3/2008

OTHER PUBLICATIONS

Daft, Wagner, P., et al. "5G-1 Two Approaches to Electronically Scanned 3D Imaging Using cMUTs." 2006 IEEE Ultrasonics Symposium. IEEE, 2006. (Year: 2006).*

(Continued)

*Primary Examiner* — Isam A Alsomiri
*Assistant Examiner* — Jonathan D Armstrong
(74) *Attorney, Agent, or Firm* — Hill & Schumacher

(57) ABSTRACT

Systems and methods are disclosed for performing imaging with a crossed-electrode ultrasound transducer array, where ultrasound transducer array is configured for focusing in one direction via conventional time-delay phased array beamforming, and for focusing in a second direction via a Fresnel aperture formed via the application of bias voltages. The ultrasound transducer array connections are switched between transmit and receive operations, such that the Fresnel aperture is generated in the first direction upon transmit, and in the second direction upon receive. One or both of the transmit Fresnel aperture and the receive Fresnel aperture are configured as a set of delay-corrected Fresnel (Continued)

sub-apertures, where the delay associated with each Fresnel sub-aperture is selected to compensate for variations in path lengths between the Fresnel sub-apertures and the focal point. The use of multiple Fresnel sub-apertures and time delay corrections overcomes problems associated with steering-induced bandwidth degradation.

27 Claims, 12 Drawing Sheets

(51) Int. Cl.
| | |
|---|---|
| G10K 11/34 | (2006.01) |
| A61B 8/00 | (2006.01) |
| A61B 8/12 | (2006.01) |
| A61B 8/08 | (2006.01) |
| B06B 1/02 | (2006.01) |
| G01N 29/26 | (2006.01) |
| G01N 29/24 | (2006.01) |
| G01S 7/52 | (2006.01) |

(52) U.S. Cl.
CPC .......... *A61B 8/4494* (2013.01); *A61B 8/5207* (2013.01); *B06B 1/0292* (2013.01); *G01N 29/2406* (2013.01); *G01N 29/262* (2013.01); *G01S 7/5202* (2013.01); *G01S 15/8915* (2013.01); *G01S 15/8925* (2013.01); *G10K 11/341* (2013.01); *G10K 11/346* (2013.01)

(56) References Cited

U.S. PATENT DOCUMENTS

| | | | | |
|---|---|---|---|---|
| 5,443,071 | A * | 8/1995 | Banjanin | A61B 8/06 600/455 |
| 5,671,746 | A | 9/1997 | Dreschel et al. | |
| 6,645,145 | B1 * | 11/2003 | Dreschel | B06B 1/00 600/443 |
| 6,656,124 | B2 | 12/2003 | Flesch et al. | |
| 6,736,779 | B1 | 5/2004 | Sano et al. | |
| 7,087,023 | B2 | 8/2006 | Daft et al. | |
| 7,474,778 | B2 | 1/2009 | Shinomura et al. | |
| 7,618,373 | B2 | 11/2009 | Ladabaum et al. | |
| 8,038,620 | B2 | 10/2011 | Lee et al. | |
| 8,125,370 | B1 * | 2/2012 | Rogers | G01S 13/904 342/25 F |
| 8,523,774 | B2 | 9/2013 | Yen et al. | |
| 8,672,850 | B1 * | 3/2014 | Miller | G10K 11/346 600/447 |
| 2003/0149363 | A1 | 8/2003 | Dreschel | A61B 8/4483 600/437 |
| 2004/0160144 | A1 * | 8/2004 | Daft | G10K 11/341 310/334 |
| 2005/0119575 | A1 * | 6/2005 | Ladabaum | B06B 1/0292 600/459 |
| 2005/0124880 | A1 | 6/2005 | Shinomura et al. | |
| 2005/0215909 | A1 * | 9/2005 | Barnes | G01S 7/52039 600/459 |
| 2005/0228277 | A1 * | 10/2005 | Barnes | G01S 7/5208 600/437 |
| 2006/0036174 | A1 * | 2/2006 | Guracar | A61B 8/483 600/458 |
| 2007/0079658 | A1 * | 4/2007 | Wagner | B06B 1/0207 73/627 |
| 2007/0194658 | A1 * | 8/2007 | Zhang | A61B 17/1325 310/314 |
| 2009/0065696 | A1 * | 3/2009 | Mann | H04B 1/40 250/339.06 |
| 2009/0076392 | A1 | 3/2009 | Oshiki et al. | |
| 2009/0079299 | A1 * | 3/2009 | Bradley | G01S 15/8927 310/322 |
| 2009/0118619 | A1 | 5/2009 | Oshiki | |
| 2009/0306510 | A1 | 12/2009 | Hashiba et al. | |
| 2012/0253198 | A1 * | 10/2012 | Hashiba | G01S 7/52095 600/447 |
| 2018/0015504 | A1 * | 1/2018 | Zhao | B06B 1/0207 |
| 2018/0154394 | A1 * | 6/2018 | Haque | A61B 8/4483 |
| 2018/0164418 | A1 * | 6/2018 | Zemp | G01S 15/8993 |
| 2018/0246207 | A1 * | 8/2018 | Brown | G10K 11/346 |
| 2018/0372691 | A1 * | 12/2018 | Zhao | G01N 29/2406 |
| 2019/0378676 | A1 * | 12/2019 | Hartley | H01J 37/045 |
| 2020/0041644 | A1 * | 2/2020 | Brown | G01S 15/8993 |

OTHER PUBLICATIONS

Daher, Nadim Michel, and Jesse T. Yen. "2-D array for 3-D ultrasound imaging using synthetic aperture techniques." IEEE transactions on ultrasonics, ferroelectrics, and frequency control 53.5 (2006): 912-924. (Year: 2006).*
Seo, Chi Hyung, and Jesse T. Yen. "5A-5 64x64 2-D Array Transducer with Row-Column Addressing." 2006 IEEE Ultrasonics Symposium. IEEE, 2006. (Year: 2006).*
Savoia, A., et al. "P2B-4 crisscross 2D cMUT array: Beamforming strategy and synthetic 3D imaging results." 2007 IEEE Ultrasonics Symposium Proceedings. IEEE, 2007. (Year: 2007).*
Siemens, "Medical Solutions", RSNA (2006).
Bezanson, A. et al., IEEE Trans. Ultrason. Ferr. and Freq. Cont. 61, 33-43 (2014).
Daft, C. et al., IEEE Ultrasonics Symposium 1578-1581 (2003).
Bezanson, A. et al., IEEE Ultrasonics Symposium 245 (2003).
Daft, C. et al., IEEE Ultrasonics Symposium 685-688 (2006).
Jensen, J., Med. & Bio. Eng. & Comp. 34, 351-353 (1996).
Jensen, J., IEEE Trans. on Ultrason. Ferro. and Freq. Cont. 39, 262-267 (1992).
Morton, C. et al., IEEE Ultrasonics Symposium 968-971 (2003).
R. E. Davidsen, J. A. Jensen, and S. W. Smith, "Two-Dimensional Random Arrays for Real Time Volumetric Imaging," Ultrason. Imaging, vol. 16, No. 3, pp. 143-163, Jul. 1994.
R. E. Davidsen and S. W. Smith, "Relaxor ferroelectric materials in two-dimensional transducer arrays," in 1995 IEEE Ultrasonics Symposium, 1995, pp. 1283-1286.
R. E. Davidsen and S. W. Smith, "Experimental results from an electrostrictive multiplexed 2-D array," in 1997 IEEE Ultrasonics Symposium, 1997, pp. 1647-1650.
International Search Report PCT/CA2016/050193 dated Jun. 16, 2016.

* cited by examiner

SYSTEMS AND METHODS OF COMBINED PHASED-ARRAY AND FRESNEL ZONE PLATE BEAMFORMING EMPLOYING DELAY-CORRECTED FRESNEL SUB-APERTURES

CROSS-REFERENCE TO RELATED APPLICATION

This application is a National Phase application claiming the benefit of the international PCT Patent Application No. PCT/CA2016/050193, filed on Feb. 25, 2016, in English, which claims priority to U.S. Provisional Application No. 62/215,548, titled "SYSTEMS AND METHODS OF COMBINED PHASED-ARRAY AND FRESNEL ZONE PLATE BEAMFORMING EMPLOYING DELAY-CORRECTED FRESNEL SUB-APERTURES" and filed on Sep. 8, 2015, the entire contents of which are incorporated herein by reference, and to U.S. Provisional Application No. 62/237,414, titled "SYSTEMS AND METHODS OF COMBINED PHASED-ARRAY AND FRESNEL ZONE PLATE BEAMFORMING EMPLOYING DELAY-CORRECTED FRESNEL SUB-APERTURES" and filed on Oct. 5, 2015, the entire contents of which is incorporated herein by reference.

BACKGROUND

The present disclosure relates to ultrasound beamforming and ultrasound imaging. In some aspects, the present disclosure relates to volumetric ultrasound imaging.

Fresnel based beam focusing has been investigated for use as a steerable lens for 3D imaging arrays. Acoustic waves, like light, can be focused using a Fresnel lens or zone plate approach. Fresnel zone plates are capable of producing a tight focus, especially when using a large aperture. A conventional Fresnel zone plate is made up of rings or strips of alternating transmissive and opaque regions. The waves diffract around the opaque zones and, because of the specific spacing, constructively interfere around the focus. In a phase zone plate, both zones transmit the wave, however, there is a phase reversal for every other zone. This type of plate has the advantage of efficiency and has shown potential to be a good approach for passive ultrasound focusing.

SUMMARY

Systems and methods are disclosed for performing imaging with a crossed-electrode ultrasound transducer array, where ultrasound transducer array is configured for focusing in one direction via conventional time-delay phased array beamforming, and for focusing in a second direction via a Fresnel aperture formed via the application of bias voltages. The ultrasound transducer array connections are switched between transmit and receive operations, such that the Fresnel aperture is generated in the first direction upon transmit, and in the second direction upon receive. One or both of the transmit Fresnel aperture and the receive Fresnel aperture are configured as a set of delay-corrected Fresnel sub-apertures, where the delay associated with each Fresnel sub-aperture is selected to compensate for variations in path lengths between the Fresnel sub-apertures and the focal point. The use of multiple Fresnel sub-apertures and time delay corrections overcomes problems associated with steering-induced bandwidth degradation.

Accordingly, in a first aspect, there is provided ultrasound imaging system comprising:

an ultrasound transducer comprising:

an array of ultrasound elements, wherein each ultrasound element is capable of acoustic transduction upon the application of a bias voltage thereto, such that the ultrasound transducer emits ultrasound energy upon the application of voltage pulses thereto when the bias voltage is present;

a first array of first electrodes provided on a first side of said array of ultrasound elements, each first electrode extending in a first direction;

a second array of second electrodes provided on a second side of said array of ultrasound elements, each second electrode extending in a second direction, wherein the first direction and the second direction are configured such that said first array of first electrodes and said second array of second electrodes are arranged in a crossed electrode configuration; and control and processing hardware operatively coupled to said ultrasound transducer, said control and processing hardware comprising processing electronics configured to perform transmit operations comprising:

providing transmit voltage pulses to said first array of first electrodes and first bias voltages to said second array of second electrodes such that an ultrasound pulse is transmitted to a focal point along a focused line of sight;

wherein the voltage pulses are provided to said first array of first electrodes such that a time delay transmit beamforming aperture is employed for focusing the ultrasound pulse to the focal point in a first plane that includes the first direction and is perpendicular of the emitting surface of the ultrasound transducer; and wherein the first bias voltages are provided to said second array of second electrodes such that a transmit Fresnel aperture is formed for focusing the ultrasound pulse to the focal point in a second plane that includes the second direction and is perpendicular of the emitting surface of the ultrasound transducer; and wherein said processing electronics are configured to perform receive operations comprising:

applying second bias voltages to said first array of first electrodes and receiving signals with said second array of second electrodes;

wherein the second bias voltages are provided to said first array of first electrodes such that a receive Fresnel aperture is formed for focusing received ultrasound energy from the focal point in the first plane;

wherein the signals obtained from said second array of second electrodes are dynamically beamformed, such that a time delay receive beamforming aperture is employed for focusing the received ultrasound energy in the second plane;

wherein said processing electronics are further configured such that one or both of the transmit Fresnel aperture and the receive Fresnel aperture are sequentially generated as a set of Fresnel sub-apertures, with the signals from the multiple transmit/receive events associated with the set of Fresnel sub-apertures being added together; and wherein said processing electronics are further configured such that:

when the transmit Fresnel aperture is generated as a set of transmit Fresnel sub-apertures, each transmit event that corresponds to a respective transmit Fresnel sub-aperture is delayed by a respective transmit time delay selected to compensate for variations in path lengths between the transmit Fresnel sub-apertures and the focal point; and when the receive Fresnel aperture is generated as a set of receive Fresnel sub-apertures, each signal corresponding to a respective receive Fresnel sub-aperture is delayed by a time delay selected to compensate variations in path lengths between the receive Fresnel sub-apertures and the focal point, prior to adding respective signals from the receive Fresnel sub-apertures together;

wherein said processing electronics are configured to perform transmit operations and receive operations along a plurality of focused lines of sight to generate ultrasound image data for producing an ultrasound image.

In another aspect, there is provided a method of performing ultrasound imaging using an ultrasound transducer:

the ultrasound transducer comprising:

an array of ultrasound elements, wherein each ultrasound element is capable of acoustic transduction upon the application of a bias voltage thereto, such that the ultrasound transducer emits ultrasound energy upon the application of voltage pulses thereto when the bias voltage is present;

a first array of first electrodes provided on a first side of said array of ultrasound elements, each first electrode extending in a first direction;

a second array of second electrodes provided on a second side of said array of ultrasound elements, each second electrode extending in a second direction, wherein the first direction and the second direction are configured such that said first array of first electrodes and said second array of second electrodes are arranged in a crossed electrode configuration;

the method comprising:

performing transmit operations by:

providing transmit voltage pulses to said first array of first electrodes and first bias voltages to said second array of second electrodes such that an ultrasound pulse is transmitted to a focal point along a focused line of sight;

wherein the voltage pulses are provided to said first array of first electrodes such that a time delay transmit beamforming aperture is employed for focusing the ultrasound pulse to the focal point in a first plane that includes the first direction and is perpendicular of the emitting surface of the ultrasound transducer; and wherein the first bias voltages are provided to said second array of second electrodes such that a transmit Fresnel aperture is formed for focusing the ultrasound pulse to the focal point in a second plane that includes the second direction and is perpendicular of the emitting surface of the ultrasound transducer; and performing receive operations by:

applying second bias voltages to said first array of first electrodes and receiving signals with said second array of second electrodes;

wherein the second bias voltages are provided to said first array of first electrodes such that a receive Fresnel aperture is formed for focusing received ultrasound energy from the focal point in the first plane;

wherein the signals obtained from said second array of second electrodes are dynamically beamformed, such that a time delay receive beamforming aperture is employed for focusing the received ultrasound energy in the second plane;

wherein one or both of the transmit Fresnel aperture and the receive Fresnel aperture are sequentially generated as a set of Fresnel sub-apertures, with the signals from the multiple transmit/receive events associated with the set of Fresnel sub-apertures being added together; and wherein one or both of the transmit Fresnel aperture and the receive Fresnel aperture are further configured such that:

when the transmit Fresnel aperture is generated as a set of transmit Fresnel sub-apertures, each transmit event that corresponds to a respective transmit Fresnel sub-aperture is delayed by a respective transmit time delay selected to compensate for variations in path lengths between the transmit Fresnel sub-apertures and the focal point; and when the receive Fresnel aperture is generated as a set of receive Fresnel sub-apertures, each set of signals corresponding to a respective receive Fresnel sub-aperture is delayed by a time delay selected to compensate variations in path lengths between the receive Fresnel sub-apertures and the focal point, prior to adding respective signals from the receive Fresnel sub-apertures;

wherein transmit operations and receive operations are performed along a plurality of focused lines of sight, thereby providing ultrasound image data for generating an ultrasound image.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which.

DETAILED DESCRIPTION

Figure 1B:
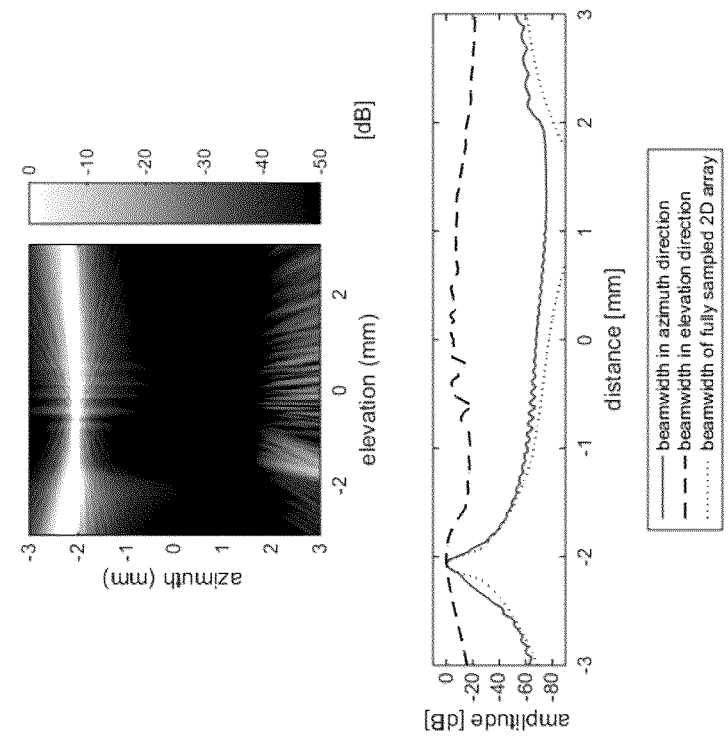
FIGS. 1A and 1B show two-way radiation pattern in the elevation-azimuth plane and beam profile for an array using a steerable Fresnel aperture in elevation and phased array beamforming in azimuth focused A) on axis and B) to 20 degrees in both planes.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise specified, the terms "about" and "approximately" mean plus or minus 25 percent or less.

It is to be understood that unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As used herein, the term "on the order of", when used in conjunction with a quantity or parameter, refers to a range spanning approximately one tenth to ten times the stated quantity or parameter.

Fresnel Zone Plates in Ultrasound Beamforming and Imaging

Implementing a Fresnel zone plate approach in an ultrasound transducer requires control of the pulse polarity. For example, arrays built on electrostrictive ceramics or capacitive micromachined transducers arrays are appropriate for this approach because the response of each array element is controlled by a DC bias. Electrostrictive ceramics such as PMN-PT (lead magnesium niobate-lead titanate) ceramic can be used as the array substrate in place of conventional piezoelectrics. This type of material is only piezoelectrically active while a bias voltage is applied and the response is tunable with the amplitude of the bias voltage. When no voltage applied the transducer, the response is negligible, and when a DC bias is applied, the phase of the acoustic wave produced is quantized to either +90 or −90 degrees, depending on whether the bias is positive or negative. Array elements defined on an electrostrictive substrate can therefore be addressed individually and in parallel. This allows for reconfigurable interferometric Fresnel zone plates to be created by varying biasing patterns.

Conventional linear-phased arrays use an acoustic lens to improve the elevational slice resolution (thickness) of the image. If an elevation lens could be reconfigured to steer to moderate angles, a 3D volumetric image could be captured without adding additional beamforming channels and only moderately increasing the number of electrical connections. This can be accomplished by replacing the mechanical acoustic lens with an electrically reconfigurable lens, which approximates a Fresnel zone plate. A Fresnel zone plate may be created by applying the appropriate pattern of positive and negative biases along the elevation direction of the array which determine the polarity of the pulses from each element.

In one example implementation, a crossed-electrode array may be formed having a set of bottom electrodes running orthogonal to the top electrodes. The bottom electrodes provide the active lens control in the elevation plane and the result is an array that requires approximately 2N electrical connections. The alternative approach to capturing 3D image volumes is to use a 2D array with $N^2$ elements. Low beamforming complexity and minimal electrical connectivity are advantages of this crossed electrode approach over other 2D array designs used in volumetric imaging.

In such a crossed electrode array configuration, the Fresnel bias pattern can be applied along the bottom electrodes (elevation direction) while the top electrodes (azimuth direction) carry the signals and are beamformed traditionally (i.e. using a conventional time delay beamforming aperture in transmit and receive, optionally using dynamic beamforming in receive). In such an example embodiment, the Fresnel pattern is directly analogous to a lens. However, by purely relying on a reconfigurable Fresnel zone plate for focusing in the elevation plane, unacceptably high secondary lobes result, preventing this technique from producing useful diagnostic images.

Figure 1A:
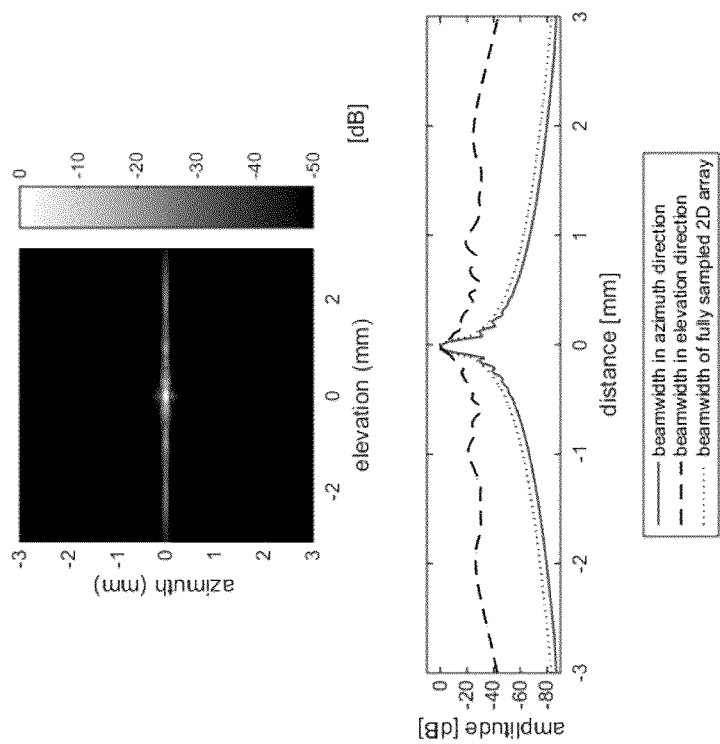

FIGS. 1A and 1B show example radiation patterns for a crossed electrode array configured such that conventional phased array time delay beamforming is used in the azimuthal plane and a reconfigurable Fresnel zone plate is used in the elevation plate. Even without steering the Fresnel zone plate (zero degrees, FIG. 1A) the secondary lobes are too high, limiting the contrast at which the image can be displayed for the array in this Figure.

Two-Way Focused Fresnel/Phased-Array Method

Figure 2:
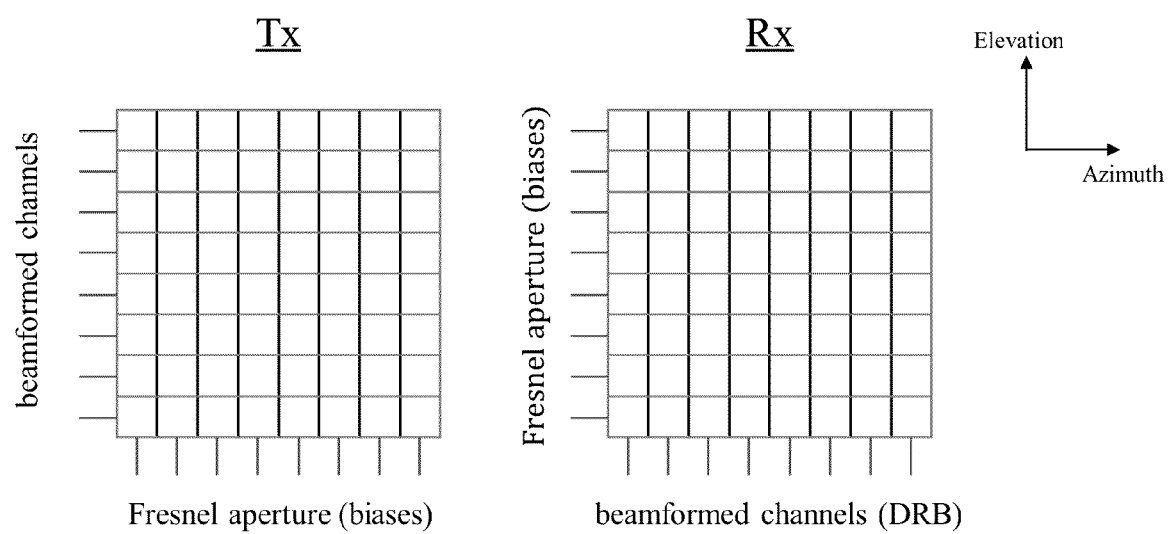
FIG. 2 shows a crossed array switching scheme for transmit and receive modes.

The radiation pattern of the array, however, can be improved by switching the positions of the bias and signal lines on the array between transmit and receive (FIG. 2) (i.e. switching the Fresnel aperture from direction to the other, while also switching the time delay beamforming aperture from one direction to the other). The Fresnel aperture in this figure would focus in azimuth on transmit while the elevational elements are beamformed using conventional time-delay beamforming (or vice versa). Between transmit and receive events, the signals switch sides. The biases are then applied in elevation for Fresnel zone plate focusing, and dynamic receive beamforming (DRB) can be completed in azimuth. An equivalent two-way focus is created in both imaging planes.

Figures 3A, 3B:
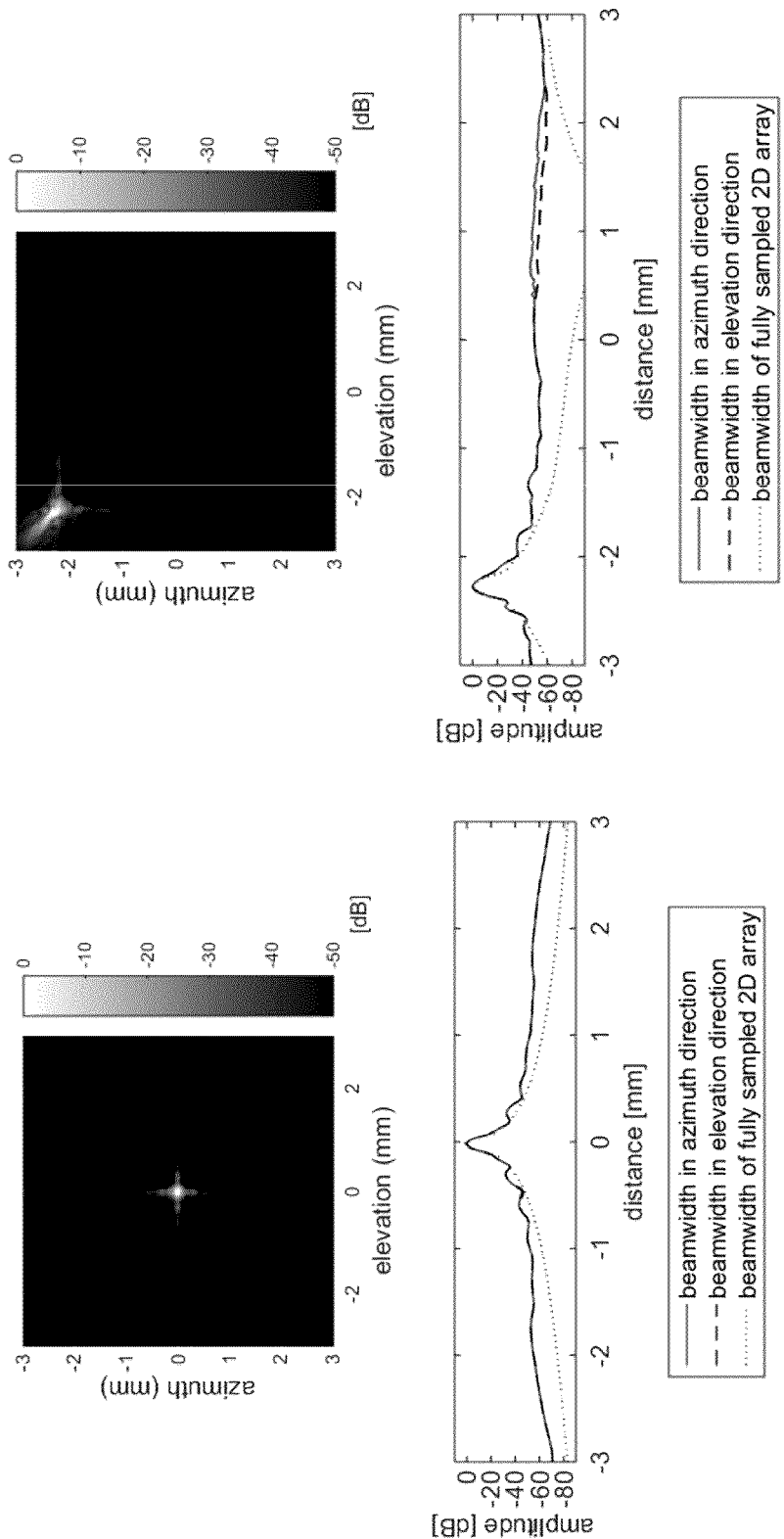
FIGS. 3A and 3B show two-way radiation pattern in the elevation-azimuth plane and beam profile for an array using a steerable Fresnel aperture focused A) on axis and B) to 20 degrees in both planes, where during transmit, the Fresnel aperture is employed for focusing in the azimuth direction and conventional phased-array beamforming is employed in the elevation direction, while during receive, the Fresnel aperture is employed for focusing in the elevation direction and conventional phased-array beamforming is employed in the azimuth direction.

Representative radiation patterns and beam profiles simulating this technique are shown in FIGS. 3A and 3B. The results were compared with a 4096 element (64×64) fully sampled and beamformed array. The −6 dB beamwidths using the Fresnel aperture were 102, 111 and 137 µm when steered to 0, 15 and 25 degrees respectively. For comparison, the 4096 element array had simulated beamwidths of 89, 92 and 96 µm for the same set of steering angles. The side lobe levels raised by approximately 15 dB using the Fresnel approach. Sensitivity remained mostly unaffected as the received energy amplitude is comparable. Switching the bias dimension with the signal dimension between transmit and receive minimizes the negative effect of the approximations made with the Fresnel aperture. Using this approach the beamwidths in azimuth and elevation are equivalent.

Additional improvements can be made by carefully choosing the Fresnel pattern. As mentioned previously, a Fresnel pattern for a given focal location is not unique. The beam characteristics can be improved for a given focal point by choosing the optimal Fresnel pattern. The Fresnel aperture simulations show that a two-way focus can be achieved in each imaging plane with beamwidths comparable to a conventionally beamformed 2D array. This steerable lens technique could generate 3D images with only N signal channels and N bias channels. Performance for the array shown in this Figure in the simulated angle range is comparable to that of a conventional 2D array that requires $N^2$ channels.

Problems with the Two-Way Focused Fresnel/Phased-Array Method

The aforementioned Fresnel approach quantizes the phase delay to two values (phase delay of $+\pi/2$ or $-\pi/2$ radians or, equivalently, a path length of $+\lambda/4$ or $-\lambda/4$). The theory for the Fresnel zone plate is based on continuous wave operation. There are challenges when applying the conventional technique to pulsed ultrasound imaging, notably, a degradation in pulse bandwidth. This is especially detrimental when steering to wide angles where the path length differences are larger: the axial resolution degrades with steering angle since the path delay between the array and the focus increases, causing increased blurring of the image towards wider steering angles.

For example, as the steering angle increases, the differences in path length from the array elements to a focal point becomes large. Even at moderate angles, the path length difference between an element and the reference path length can be many multiples of the wavelength (e.g., at 20 degrees, up to 10 wavelengths). When all elements are pulsed at the same time, path length differences can only be corrected within one wavelength; thus the pulses at the focus do not overlap and the resulting constructively interfered pulse is stretched out in time (narrow band). A narrowband pulse such as this is not acceptable for imaging since the axial resolution is proportional to the length of the pulse.

Two-Way Focused Fresnel/Phased-Array Method Via Split-Aperture Fresnel Beamforming with Delay Correction In some example embodiments, a crossed-electrode transducer may be configured for imaging using the two-way focusing method described above (switching the bias and signal connections between transmit and receive), with the further modification that one or both of the transmit Fresnel aperture and the receive Fresnel aperture are configured as a set of delay-corrected Fresnel sub-apertures. Unlike the aforementioned examples employing a single Fresnel aperture, the present example embodiments employ a set of Fresnel sub-apertures during separate and sequential transmit/receive events, where the timing of transmit and/or receive operations involving the Fresnel sub-apertures corrects for path length variations between the sub-apertures and the focal point, thus shortening the pulse length of each transmitted pulse (i.e. broadening the bandwidth) at the focus. This modification can therefore be employed to address and overcome the aforementioned limitations pertaining to steering-induced bandwidth degradation.

Figure 4A:
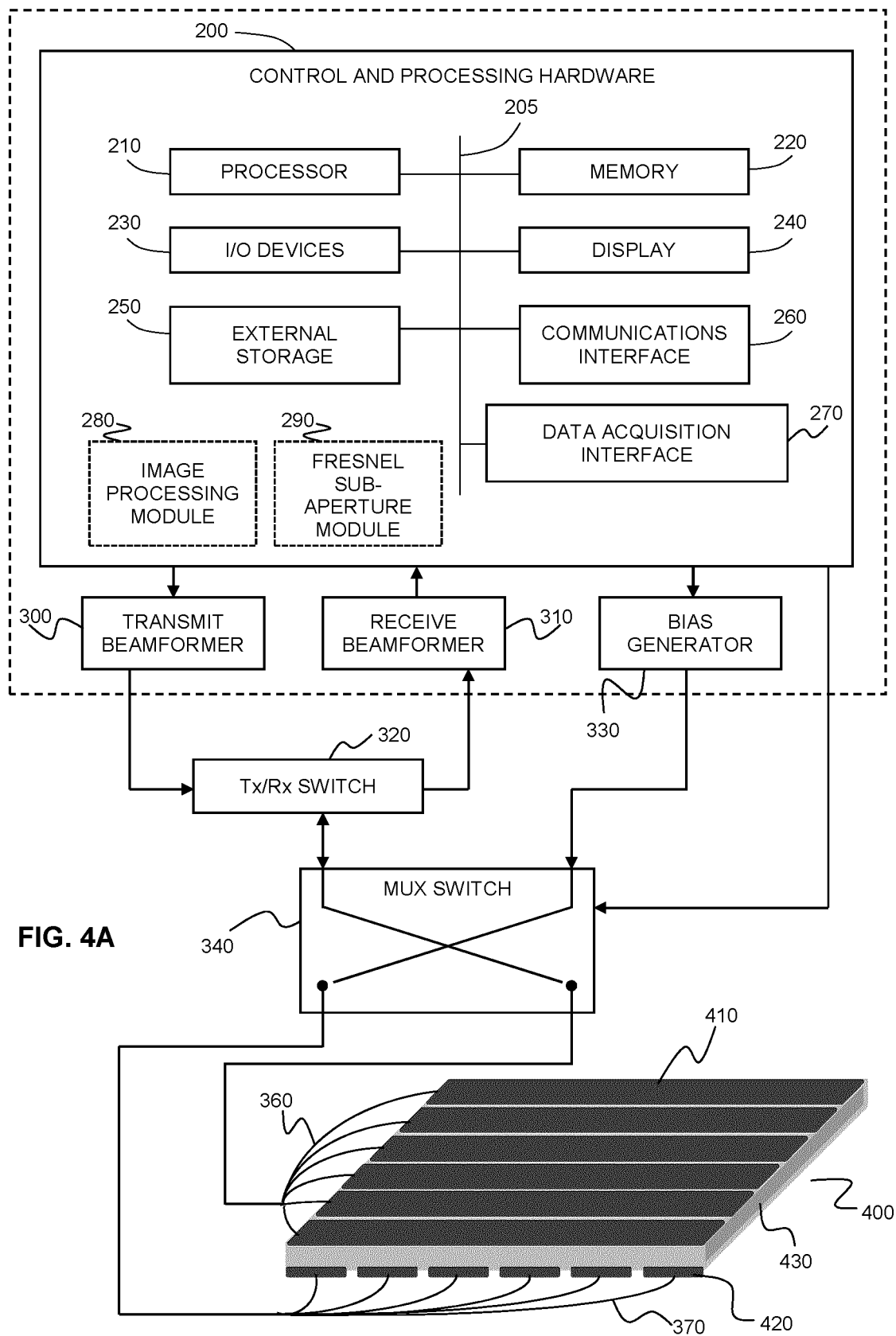
FIG. 4A illustrates an example imaging system involving a crossed-electrode transducer.

Referring now to FIG. 4A, an example imaging system for performing cross-electrode based, two-way focused imaging with delay-corrected multiple Fresnel sub-apertures is illustrated. The example system includes a crossed-electrode ultrasound transducer 400 (which may be a component of an ultrasound imaging device, such as an ultrasound imaging endoscope), a transmit beamformer 300 with pulser-receiver circuitry 320, a receive beamformer 310, a bias generator 330, MUX switch 340, and control and processing hardware 200 (e.g. a controller, computer, or other computing system).

Figure 4B:
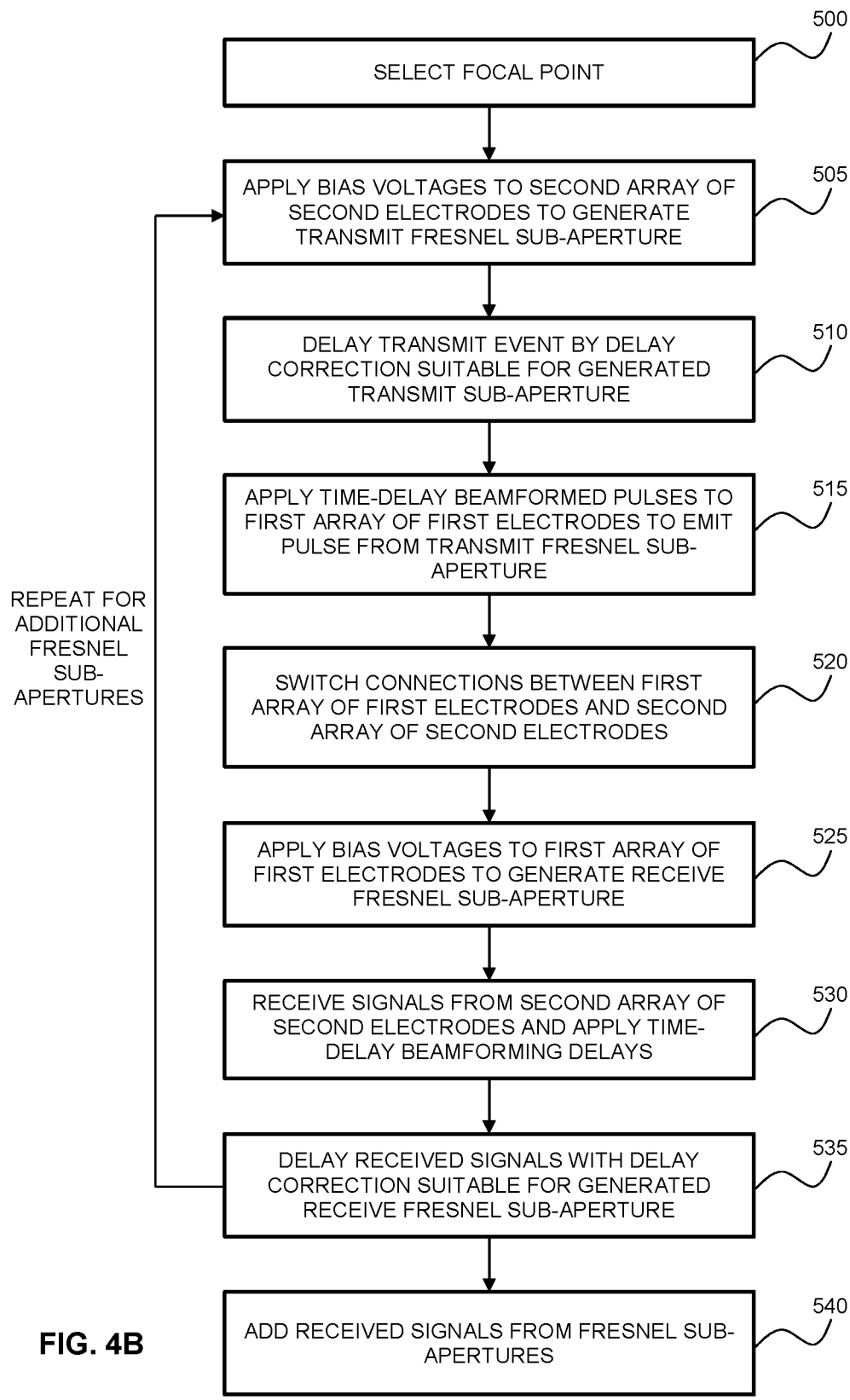
FIG. 4B is a flow chart showing an example method of employing multiple Fresnel sub-apertures in transmit and receive for a given line of sight.

Control and processing hardware 200 is employed to control transmit beamformer 300 and receive beamformer 310, MUX switch 340, and for processing the beamformed receive signals. As shown in FIG. 4, in one embodiment, control and processing hardware 200 may include a processor 210, a memory 220, a system bus 205, one or more input/output devices 230, and a plurality of optional additional devices such as communications interface 260, display 240, external storage 250, and data acquisition interface 270.

An example of crossed electrode ultrasound transducer 400 is disclosed in US Patent Application No. US 2007/0079658 (Wagner), titled "ROTATING APERTURE FOR ULTRASOUND IMAGING WITH A CAPACITIVE MEMBRANE OR ELECTROSTRICTIVE ULTRASOUND TRANSDUCER". In FIG. 4, another example of a crossed-electrode ultrasound transducer is shown including, on either sides of an electrostrictive layer 430, a first array of first electrodes 410 and a second array of second electrodes 420. First electrodes 410 extend in a first direction, and second electrodes 420 extend in a second direction. First electrodes 410 are employed for focusing ultrasound energy in a first plane that is perpendicular to an emitting surface of the ultrasound transducer, and includes the first direction. Second electrodes 420 are employed for focusing ultrasound energy in a second plane that is perpendicular to an emitting surface of the ultrasound transducer, and includes the second direction. The first and second planes may be perpendicular in order to enable scanning in orthogonal directions (e.g. azimuth and elevation).

In the present example implementation, first electrodes 410 and second electrodes 420 are shown in a perpendicular crossed configuration, although in other example implementations, the electrodes can be provided in a crossed configuration with an angle of other that 90 degrees. Furthermore, although the figure shows the first and second electrodes as longitudinal electrodes, it will be understood that the electrodes need not be strictly linear in shape, provided that the first electrodes extend in the first direction and the second electrodes extend in the second direction and define linear arrays of ultrasound elements in two dimensions.

It will be understood that although the figure shows an example implementation involving an unkerfed layer of electrostrictive material as the ultrasound transduction layer, other materials and configurations may be employed. For example, the ultrasound transduction layer may be a kerfed array of electrostrictive array elements, or an array of capacitive micromachined ultrasound transducers, both of which, like the unkerfed electrostrictive layer, are capable of acoustic transduction upon the application of a bias voltage, such that the ultrasound energy is emitted upon the application of voltage pulses when the bias voltage is present.

The first array of first electrodes 410 and the second array of second electrodes 420 are in electrical communication with separate outputs of MUX switch 340 via conductors 360, such that during transmit, the first array of first electrodes are in electrical communication with the transmit beamformer 300 via the Tx/Rx switch 320, and such that transmit voltage pulses are provided to the first array of first electrodes for focusing an ultrasound pulse via conventional time-delay transmit beamforming. As noted above, the first array of first electrodes focus the ultrasound pulse in the first plane. Furthermore, during transmit, the bias generator 330 applies biases to the second array of second electrodes 420 via conductors 370, such that the ultrasound pulse is focused within the second plane via a Fresnel aperture.

The MUX switch 340 is activated by control and processing hardware 200 prior to performing a receive operation, switching the bias and signal connections from transmit and receive. The second array of second electrodes 410 are brought into electrical communication with the receive beamformer 300 via the Tx/Rx switch 320, such that ultrasound signals are received along the selected line of sight by the second array of second electrodes for focusing an ultrasound pulse via conventional time-delay receive beamforming (optionally via dynamic receive beamforming). Furthermore, during receive, the bias generator 330 applies biases to the first array of first electrodes 420 via conductors 370, such that the receive ultrasound signals are focused within the second plane via a Fresnel aperture.

As explained above, the present example embodiments involve the use of Fresnel sub-apertures during transmit and/or receive. For each Fresnel sub-aperture, bias voltages are applied to a subset of electrodes such that portion of the Fresnel pattern is formed, where the full Fresnel aperture is configured generate a focus a the desired steering angle (along a desired line of sight).

In the present example embodiment, in order to avoid the aforementioned problems associated with the unwanted effects of a pulse stretching out in time, an additional delay may be added when a given Fresnel sub-aperture is used in transmit and/or receive. For any given sub-aperture, an additional delay is provided that compensates for variations in the path lengths between the transmit Fresnel sub-apertures and the focal point. The additional delay therefore compensates for the limitation of the Fresnel technique being quantized to path lengths of $+\lambda/4$ or $-\lambda/4$. As described below, the additional delay may be added when Fresnel sub-apertures are employed in transmit and/or in receive. In one example implementation, the delays for the respective Fresnel sub-apertures may be determined by calculating the path length differences between the center of each Fresnel sub-aperture (or some other location associated with each Fresnel sub-aperture) and the focal point, and generating the delays to compensate for differences in the path lengths among the sub-apertures.

The transmit Fresnel aperture, formed by applying the bias voltages to the second array of second electrodes, may be implemented as a set of transmit Fresnel sub-apertures, where each transmit Fresnel sub-aperture has a separate and sequentially activated transmit/receive event associated therewith, and where an additional delay is added for each transmit event in order to compensate for path-length variations, as explained above. The receive Fresnel aperture, formed by applying bias voltages to the first array of first electrodes, may additionally or alternatively be implemented as a set of receive Fresnel sub-apertures, where each receive Fresnel sub-aperture has a separate and sequentially activated transmit/receive event associated therewith, and where an additional delay is added for each receive event in order to compensate for path-length variations, as explained above. An example method involving the use of Fresnel sub-apertures for both transmit and receive is illustrated in the flow chart shown in FIG. 4B.

After having performed the aforementioned method for a single line of sight/focal point, the method may be repeated for additional lines of sight, in order to collect a data set for generating an image (such as a volumetric image). An image processing module 280 may then process the data set in order to render an image, for example, using scan conversion methods.

Figure 5A:
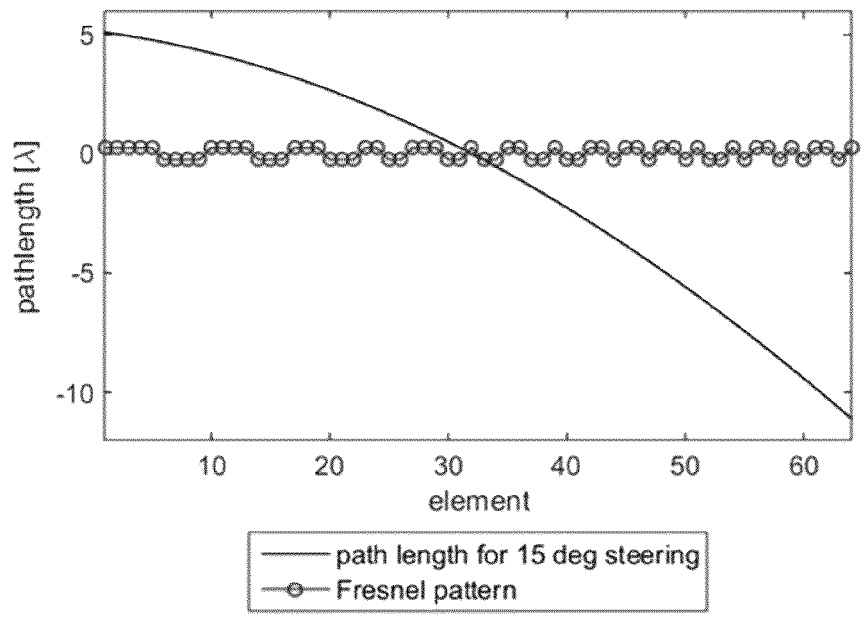
FIGS. 5A and 5B depict (A) a comparison between the path length from the sub-aperture to a focal point and the effective path length caused by the Fresnel sub-apertures, and (B) a comparison between the path length from the sub-aperture to a focal point and the effective path length caused by the Fresnel sub-apertures with the additional corrective delay. The example relates to a Fresnel pattern divided into 4 sub-apertures.
Figure 5B:
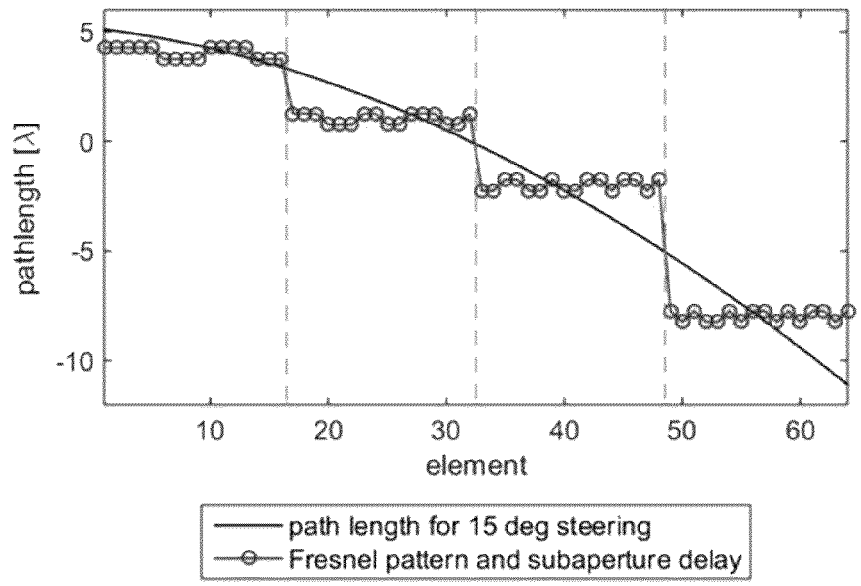

The use of a quantized Fresnel pattern for the Fresnel sub-apertures, with the additional delay compensation as described above, results in the pulses transmitted and/or received from the different Fresnel sub-apertures experiencing a similar or equal effective path length. This delay-mediated path-length compensation for the Fresnel sub-apertures is illustrated in FIGS. 5A and 5B. FIG. 5A shows a plot of the difference in path length between a distal focal point and each array element when the additional delay is absent, comparing this difference with the relatively flat, $\lambda/4$ quantized effective path length difference generated by the phase lag of the Fresnel pattern alone (the present example show a four-sub-aperture delay corrected configuration). In stark contrast to FIG. 5B shows the close correspondence between the element-to-focal-point path length difference and the effective path length difference produced by the combination of the Fresnel pattern and the delay correction that is employed for each Fresnel sub-aperture.

Among other advantages, the use of path length compensated Fresnel sub-apertures in transmit and/or receive results in the preservation of pulse bandwidth at larger steering angles, which corrects for the beamforming errors otherwise inherent in the Fresnel approach. When the respective signals from the multiple transmit/receive events associated with each sub-aperture are added together on receive, also compensating for aperture path length variations using per-sub-aperture delay corrections as described above, the received echo maintains a broad bandwidth without compromising the desired radiation pattern and lateral resolution. The resulting pulse length using such an embodiment is reasonable for phased array imaging at a wide range of steering angles.

Figure 6A:
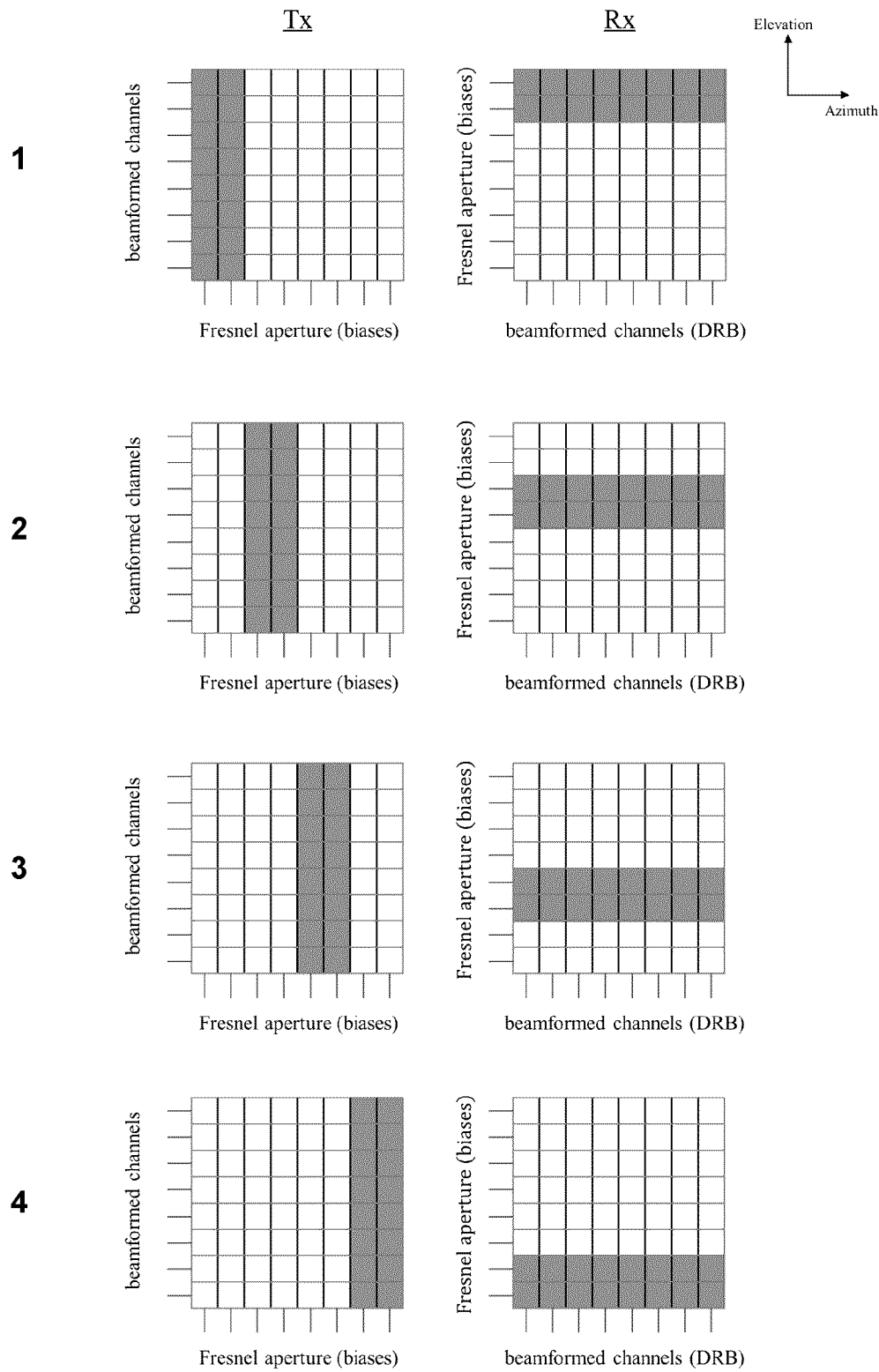
FIG. 6A depicts an example implementation in which Fresnel sub-apertures are employed in both transmit and receive, and wherein a single unique receive Fresnel sub-aperture is generated for each transmit Fresnel sub-aperture, and where 4 sup-apertures are employed for transmit and 4 sub-apertures are employed for receive, in an 8×8 crossed electrode array.

In some embodiments, Fresnel sub-apertures and path length delay correction may be employed in both transmit and receive, as noted above. FIG. 6A illustrates an example implementation involving the use of Fresnel sub-apertures in both transmit and receive for an 8×8 crossed-electrode array. In the present example implementation, Fresnel sub-apertures are defined in both transmit and receive based on a pair of adjacent electrodes, such that four Fresnel sub-apertures are used in each of transmit and receive. A total of four transmit/receive events are employed for each line of sight. In the first transmit/receive event, the leftmost azimuth Fresnel sub-aperture is employed in transmit and the topmost elevation Fresnel sub-aperture is employed in receive. Both the transmit and receive Fresnel sub-apertures are shifted during subsequent transmit/receive events, such that all transmit Fresnel sub-apertures and all receive Fresnel sub-apertures are employed using a compact sequence involving only four transmit/receive events. In the present example embodiment, the number of transmit Fresnel sub-apertures equals the number of receive Fresnel sub-apertures.

Figure 6B:
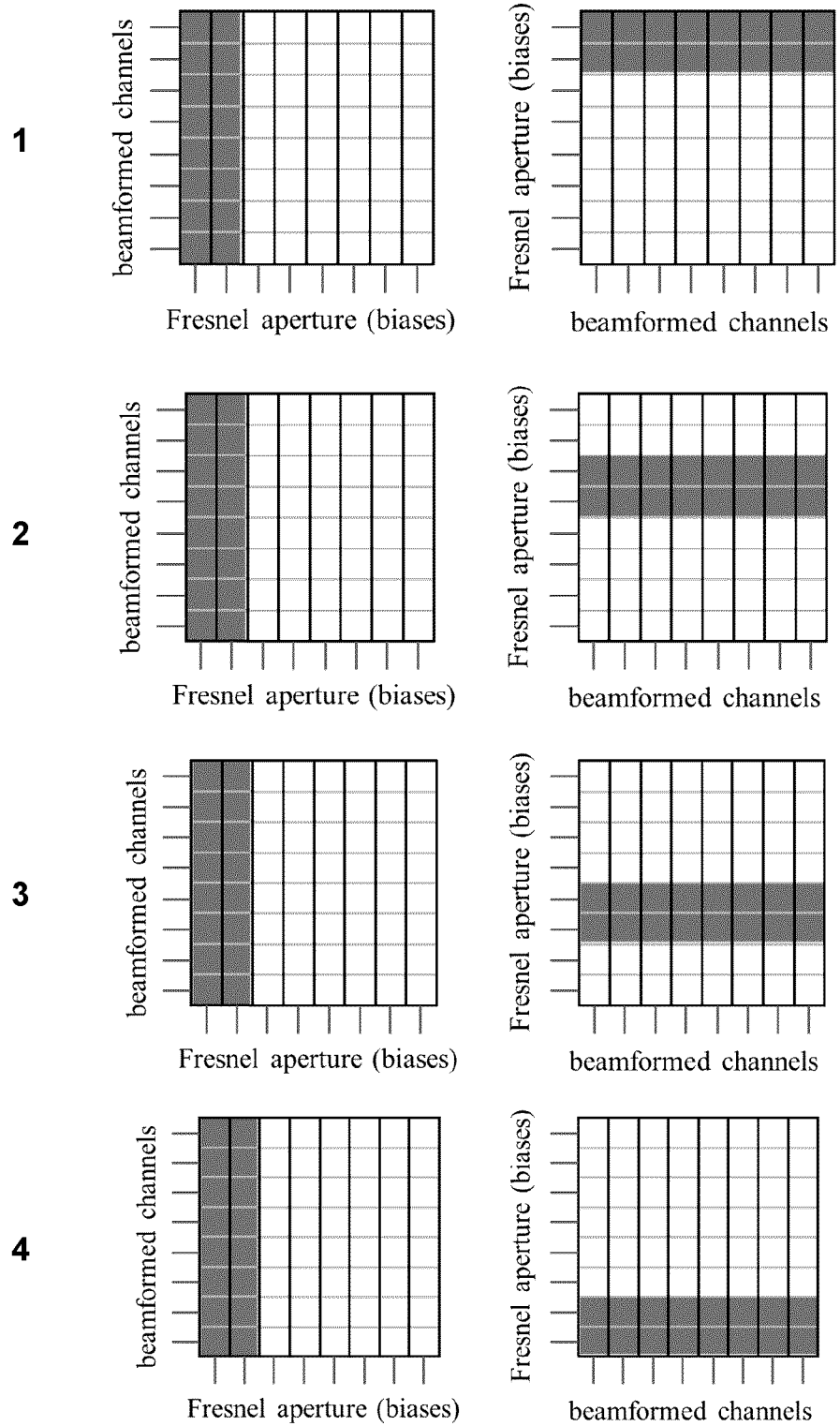
FIG. 6B depicts an example implementation in which Fresnel sub-apertures are employed in both transmit and receive, where 4 sup-apertures are employed for transmit and 4 sub-apertures are employed for receive, in an 8×8 crossed electrode array. The figure shows the combination of transmit and receive Fresnel sub-apertures that correspond to transmit/receive events associated with the first transmit Fresnel sub-aperture. Similar transmit/receive events are then performed for the additional transmit Fresnel sub-apertures, such that for each transmit Fresnel sub-aperture, a set of transmit/receive events are performed for each of the receive Fresnel sub-apertures.

FIG. 6B illustrates an alternative example implementation involving the use of Fresnel sub-apertures for both transmit and receive operations, where, for a given line of sight, a sequence of transmit/receive events are performed using all combinations of transmit Fresnel sub-apertures and receive Fresnel sub-apertures. FIG. 6B shows a first set of four transmit/receive events, where the set of all receive Fresnel sub-apertures and employed for a first (leftmost azimuth) transmit aperture. An additional 12 transmit/receive events would subsequently be performed, such that transmit/receive events are performed for each of the three remaining transmit Fresnel sub-apertures, such that four transmit/receive events are performed for each remaining transmit Fresnel sub-aperture corresponding to all four receive Fresnel apertures. It will be understood that the sub-aperture configurations and sequences shown in FIGS. 6A and 6B are merely provided as examples, and that other numbers of transmit and receive Fresnel sub-apertures, and other sub-aperture sequences, may alternatively be employed.

In some example embodiments, when Fresnel sub-apertures are employed for both transmit and receive, the number of transmit Fresnel sub-apertures need not equal the number of receive Fresnel sub-apertures. For example, lateral resolution may be reduced in one direction by using fewer Fresnel sub-apertures than in the other direction.

The present example methods of performing transmit/receive operations using Fresnel sub-apertures can be implemented via processor 210 and/or memory 220. As shown in FIG. 4, the control of the Fresnel sub-apertures, including the selection of the sub-apertures and the control of the timing of transmit/receive events associated with the Fresnel sub-apertures, may be implemented by control and processing hardware 200, via executable instructions represented as Fresnel sub-aperture module 290. The control and processing hardware 200 may include and execute scan conversion software (e.g. real-time scan conversion software).

The functionalities described herein can be partially implemented via hardware logic in processor 210 and partially using the instructions stored in memory 220. Some embodiments may be implemented using processor 210 without additional instructions stored in memory 220. Some embodiments are implemented using the instructions stored in memory 220 for execution by one or more general purpose microprocessors. Thus, the disclosure is not limited to a specific configuration of hardware and/or software.

In some embodiments, the plurality of Fresnel sub-apertures that are defined may together equal the area of the transducer aperture. In some embodiments, the sub-apertures are equal rectilinear regions of array elements.

In one example implementation, the Fresnel sub-apertures may be defined as equal rectilinear regions and the sum of the regions may be equal in area to that of the transducer aperture. In another example implementation, the Fresnel sub-apertures may be defined as two or more unequal rectilinear regions and the sum of the regions may be equal in area to that of the transducer aperture.

In another example implementation, the Fresnel sub-apertures may be defined as equal rectilinear regions and the sum of the regions may be equal to an area less than the transducer aperture, so that only a portion of the transducer aperture is employed to generate the full Fresnel aperture. In another example implementation, the Fresnel sub-apertures may be defined as two or more unequal rectilinear regions and the sum of the regions may be equal to an area less than transducer aperture, so that only a portion of the transducer aperture is employed to generate the full Fresnel aperture.

In one example implementation, the Fresnel sub-apertures may represent sub-sections of a Fresnel pattern, such that the sub-sections collectively correspond to the Fresnel-type aperture based on the Fresnel pattern.

In another example implementation, the Fresnel sub-apertures may represent sub-sections of a Fresnel pattern, such that the sub-sections collectively correspond to a Fresnel pattern that is different than that of the Fresnel-type aperture based on the Fresnel pattern.

In some example implementations, one or more Fresnel sub-apertures may involve at least two rows or columns of array elements. In some example implementations, each Fresnel sub-aperture involves at least two rows or columns of array elements.

In some embodiments, the Fresnel sub-apertures are defined top-to-bottom across the array. In some embodiments, the Fresnel sub-apertures are defined left-to-right across the array. In some embodiments, the set of Fresnel sub-apertures used may be defined top-to-bottom in receive mode and left-to-right in transmit mode, or vice versa. In some embodiments, there are at least 8 Fresnel sub-apertures. In some embodiments, there are between 6 and 8 Fresnel sub-apertures. In some embodiments, there are between 4 and 8 Fresnel sub-apertures. In some embodiments, there are between 3 and 8 Fresnel sub-apertures.

In some embodiments, the number of Fresnel sub-apertures may be dynamically configured based on the imaging angle in the Fresnel imaging plane. For example, the number of Fresnel sub-apertures may be increased as the steering angle increases. The number of Fresnel sub-apertures may increase with the increase in steering angle at a rate suitable for producing a consistent image with respect to resolution. A dependence of the number of sub-apertures on steering angle may be programmed in control and processing hardware 200, such that bias generator 330 can be dynamically controlled by control and processing hardware 200 in order to generate a suitable number of Fresnel sub-apertures.

For example, when focusing in front of the array, only one or two Fresnel sub-apertures may be required to achieve a broadband pulse. This is because the path length difference across the array is small in for this case, for example, only about two wavelengths. As the steering angle is increased, large path lengths across the array result and hence more Fresnel sub-apertures shifted by one wavelength are required to maintain a broad band pulse.

It will be understood that the number of sub-apertures to be defined for a given imaging application may depend on a number of factors, including the application, the magnitude of the steering angle or angles to be focused, the volume to be imaged, and the desired frame rate.

In embodiments using crossed electrode arrays, the number of transmit/receive events, and, therefore, total collection time, is related to the number of imaging lines in the elevational and azimuthal directions and the average number of sub-apertures used. For example, if there are 64 imaging lines in both directions and an average of 6 sub-apertures (averaged over the multiple lines of sight corresponding to different steering angles when the number of Fresnel sub-apertures is dependent on the steering angle) it would take 24,576 transmit/receive events to capture a volume, which for a 12 mm imaging depth would result in a frame rate of about 2.5 Hz. In some embodiments, a smaller volume can be imaged by limiting the sector angle in elevation; fewer transmit/receive events would then be required because there would be fewer imaging lines and the average number of sub-apertures would also decrease.

Referring again to FIG. 4, it is to be understood that the example system shown in the figure is not intended to be limited to the components that may be employed in a given implementation. For example, the system may include one or more additional processors. Furthermore, one or more components of control and processing hardware 200 may be provided as an external component that is interfaced to a processing device. For example, as shown in the figure, any one or more of transmit beamformer 300, receive beamformer 310, and bias generator 330 may be included as a component of control and processing hardware 200 (as shown within the dashed line), or may be provided as one or more external devices. Transmit beamformer 300, receive beamformer 310, image processing module 280, and delay generation module 290 may be configured or programmed to execute algorithms for performing the methods described herein.

While some embodiments can be implemented in fully functioning computers and computer systems, various embodiments are capable of being distributed as a computing product in a variety of forms and are capable of being applied regardless of the particular type of machine or computer readable media used to actually effect the distribution.

At least some aspects disclosed herein can be embodied, at least in part, in software. That is, the techniques may be carried out in a computer system or other data processing system in response to its processor, such as a microprocessor, executing sequences of instructions contained in a memory, such as ROM, volatile RAM, non-volatile memory, cache or a remote storage device.

A computer readable storage medium can be used to store software and data which when executed by a data processing system causes the system to perform various methods. The executable software and data may be stored in various places including for example ROM, volatile RAM, nonvolatile memory and/or cache. Portions of this software and/or data may be stored in any one of these storage devices. As used herein, the phrases "computer readable material" and "computer readable storage medium" refers to all computer-readable media, except for a transitory propagating signal per se.

EXAMPLES

The following examples are presented to enable those skilled in the art to understand and to practice embodiments of the present disclosure. They should not be considered as a limitation on the scope of the disclosure, but merely as being illustrative and representative thereof.

Example 1: Simulation of Pulse Bandwidth with Sub-Apertures

A bias value for each element in a Fresnel-type array is calculated by considering the geometric path length between the element and the focus. The relative phase delay for that element is given by (1).

$$\varphi = 2\pi [z - \sqrt{x^2+y^2+z^2}]/\lambda \tag{1}$$

Where x, y and z are the coordinates of the desired focus relative to the array element and $\lambda$ is the wavelength of the center frequency of the excitation pulse in the medium. The sign of the bias ($S_{bias}$) is given by (2).

$$S_{bias} = \text{sign}[\text{mod}(\varphi+\text{offset},-2\pi)-\pi] \tag{2}$$

Here we are approximating the relative phase delay for each element as the portion that falls within a single wavelength (quantized as shifted by $-\pi/2$ or $-\pi/2$ radians). This models the purely transparent regions and the pulse inverted regions of the zone plate. An offset phase can be added in the calculation that shifts the reference phase of the center element. Consequently, there is not one unique Fresnel pattern for a given focal point. The pattern can be chosen to optimize different beam shapes (e.g. main lobe width, side lobe level, sensitivity).

Field II was used to simulate the Fresnel aperture as a steerable lens to illustrate the potential of the imaging techniques. The Fresnel aperture was simulated by setting the apodization values to correspond to the sign of the bias for each element as described above. All simulations were completed for a 40 MHz example array with $\lambda$ pitch, 64 azimuthal elements and 64 elevational elements similar to a previously developed 40 MHz endoscope. The peak absolute pressure is plotted in the radiation patterns.

Figure 7:
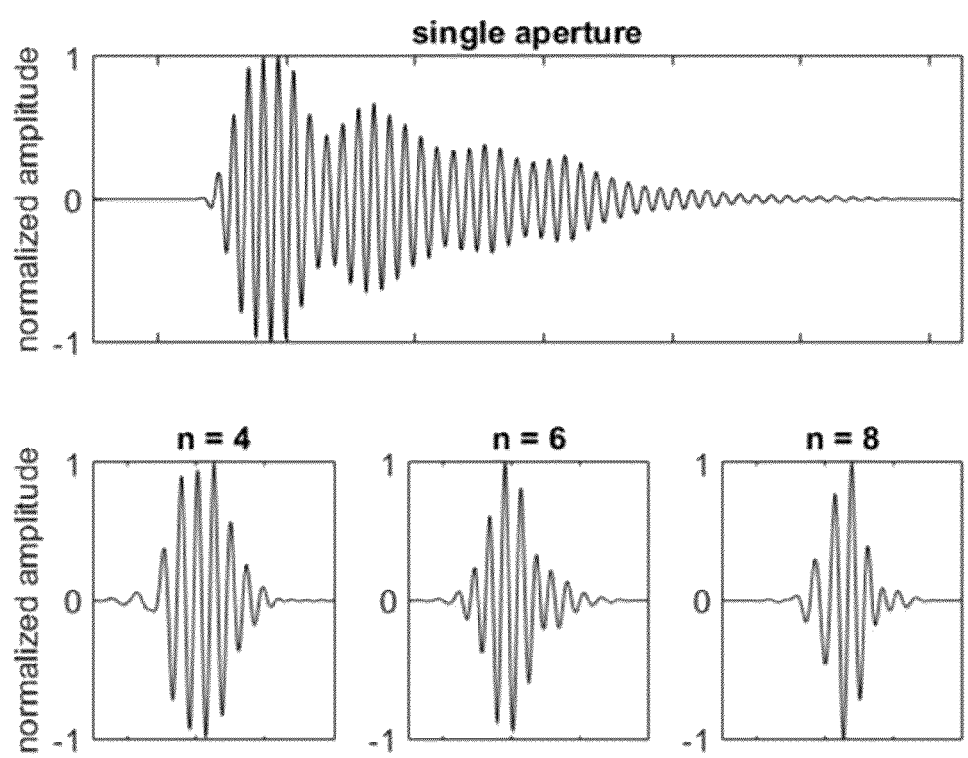
FIG. 7 shows simulated results for (top) pulse at the focus of a crossed electrode array using switching Fresnel focusing, steered to 20 degrees in azimuth and 20 degrees in elevation (bottom) pulse at the focus of this array when using 4, 6 or 8 sub-apertures respectively (bottom).

Various numbers of sub-apertures were defined in conjunction with a crossed electrode array as described above, in a simulation using the Field II software package. When focusing on-axis (0 degrees steering angle) the pulse bandwidth was calculated to be 36%. At a steering angle of 15 degrees the pulse bandwidth was calculated to be 8%, 27% and 36% when using 1 aperture, 4 sub-apertures and 8 sub-apertures. The beamwidth also improved from 111 μm with a single aperture to 97 μm when using 8 sub-apertures. The decrease in pulse length is shown in FIG. 7.

Example 2: Comparison of Fresnel Aperture/Crossed Electrode Array with Full Transmit/Receive Synthetic Aperture (SA) Imaging Implementing a Fresnel aperture on a crossed electrode array, as described above, has advantages over full transmit/receive synthetic aperture (SA) imaging. The synthetic aperture technique focuses at all points in the image, however it has two main disadvantages: 1) the small size of an active element and 2) the large number of transmit/receive events required to image a volume.

Figure 8A:
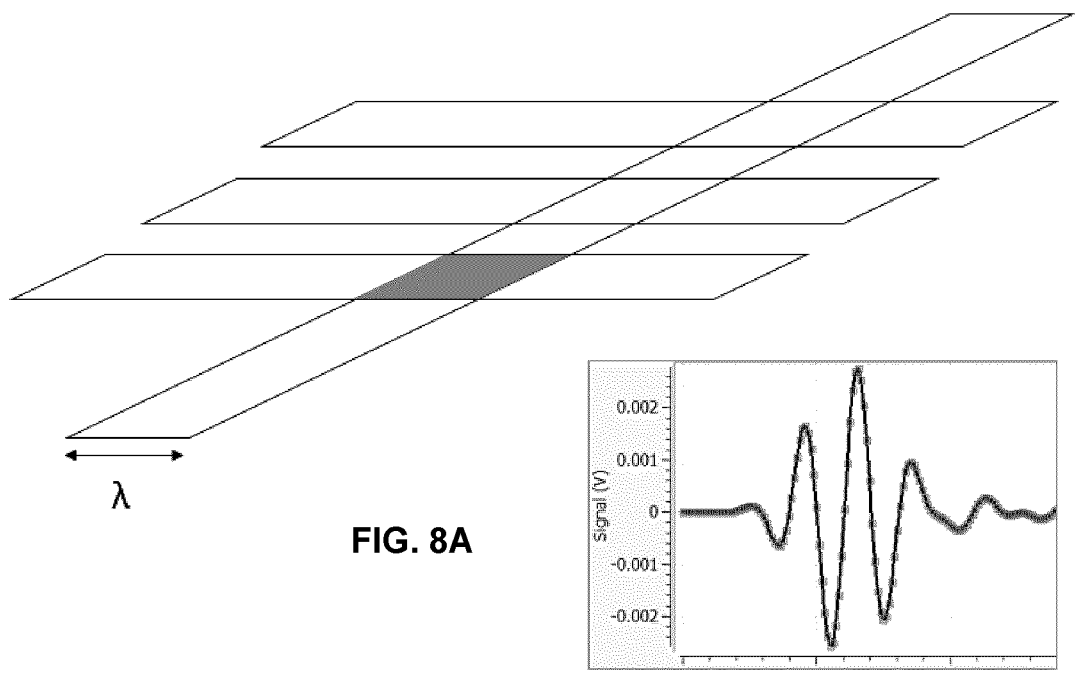
FIGS. 8A and 8B show (A) an active array and pulse echo using SA vs (B) a full crossed electrode row/column.
Figure 8B:
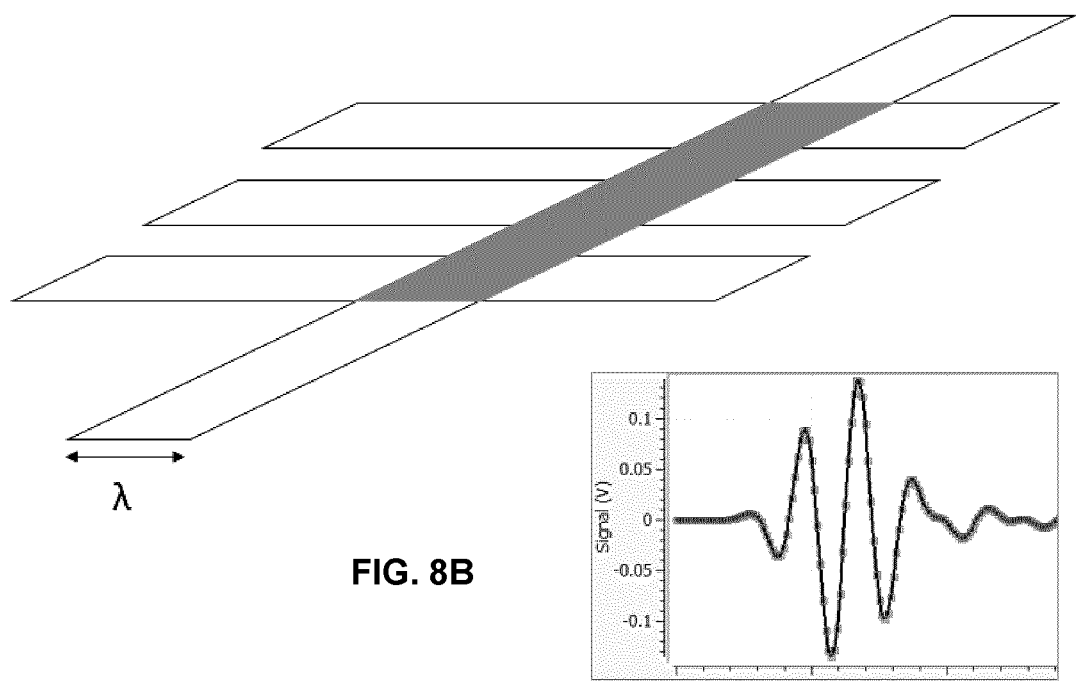
Figure 9A:
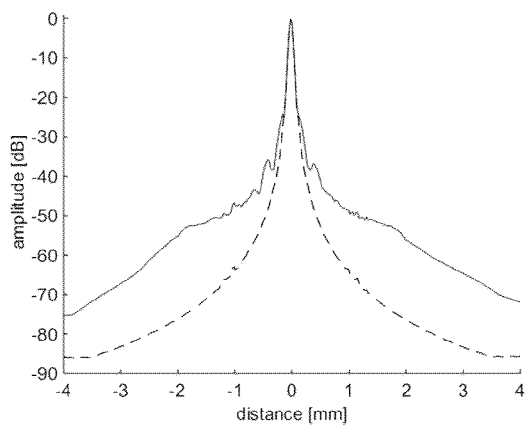
FIGS. 9A-D compare a sub-aperture Fresnel-type technique as described herein and in Example 2 for (A) 0 degree and (C) 25 degree steering angles with a switching SA technique as described in Example 2 for (B) 0 degree and (D) 25 degree steering angles. Each profile is compared to that of a fully sampled, conventionally beamformed 2D array (black dashed line).
Figure 9B:
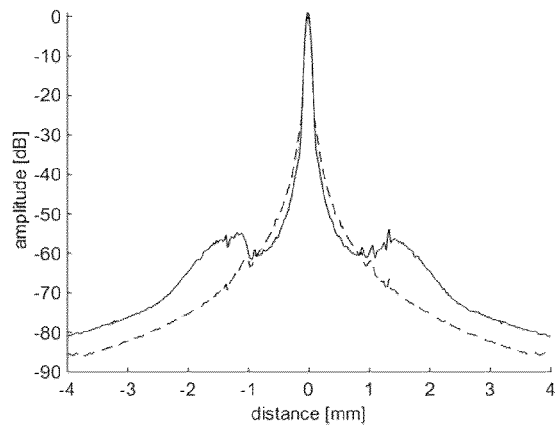
Figure 9C:
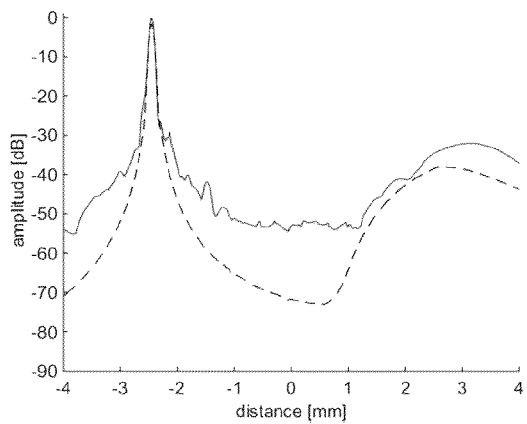
Figure 9D:
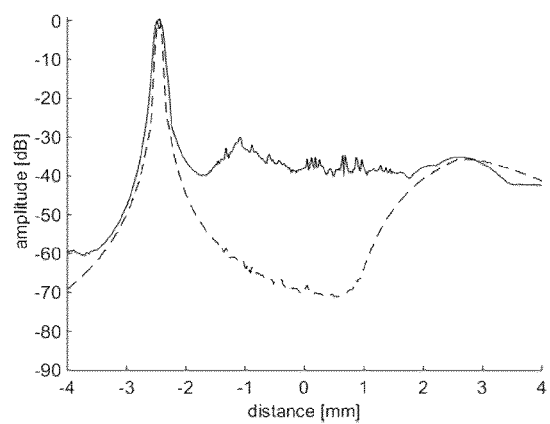

Full synthetic aperture requires pulsing a single element to create a defocussed pulse. The element impedance is inversely proportional to active area. A single element has a very large impedance and, consequently, electrical matching and sensitivity issues. When an entire row or column of a crossed electrode is active the area is N times larger which means the impedance is N times lower. For illustration, two array elements were simulated using a KLM model. The first element was $\lambda \times \lambda$ in dimension and the second was $\lambda \times N\lambda$, representing a synthetic aperture single element and a row/column of a crossed electrode array respectively (FIGS. 8A and 8B). The source and load impedance was modelled as 50Ω. The number of elements, N, was set to 64 to match the simulated array above. As expected, the smaller element has an impedance 64 times greater than the large element (6.5 kΩ vs. 102Ω). Also, the insertion loss for the small element is 34 dB greater than for a full row or column element.

The number of transmit/receive events (or frame rate) is another advantage of the Fresnel approach over conventional synthetic aperture imaging with a crossed electrode array. In conventional synthetic aperture imaging, a single element is pulsed and all elements receive in parallel. The process is then repeated by pulsing individual elements across the array. The delays required to focus at all points in the image are added after data collection and potentially results in a relatively fast frame rate. In a crossed electrode array, however, signals cannot be collected from every top and bottom array element in parallel. To acquire all of the data required for SA imaging therefore, the bottom electrodes (columns) must be multiplexed adding N receive events for each defocused transmit/receive event. The total number of transmit/receive events required in a conventional SA approach for a crossed electrode array is $N^3$. The number for transmit/receive events generally exceeds what is required for the methods described herein: approximately $N^2$*[number of sub-apertures].

A second synthetic aperture technique was considered as a comparison to the Fresnel technique described above. In a similar way to the Fresnel technique, conventional beamforming can be completed in one plane during transmit, and then switched to the other plane in receive. This technique was effective since the two-way focus is a combination of one-way conventional beamforming (high quality) and one-way Fresnel focusing (low-quality). Likewise, by switching the top and bottom electrodes, an image can be generated with a combination of one-way conventional beamforming and one-way synthetic aperture (such an example embodiment need not employ an ultrasound transduction material that is depending on a voltage bias for transduction). One can then degrade the quality of the one-way synthetic aperture focus but still by grouping elements into small defocusing sub-apertures. By doing this, the total number of transmit/receive events is traded off against focusing quality. Similar to switching the Fresnel lens however, the combination between high and low quality focusing results in acceptable radiation patterns. Simulated beam profiles for the SA imaging scheme are compared to the methods described herein in FIGS. 9A-D. For simplicity, the simulations were completed in only one plane using a 1D array. In this simulation, 4 elements were grouped to form 16 sub-apertures, effectively creating 4λ wide elements for the synthetic aperture. Because the methods describe herein only require on average approximately 6-8 sub-apertures, the SA with 16 sub-apertures would take 7.1 times longer to create the 3D image with comparable resolution.

Figure 10A:
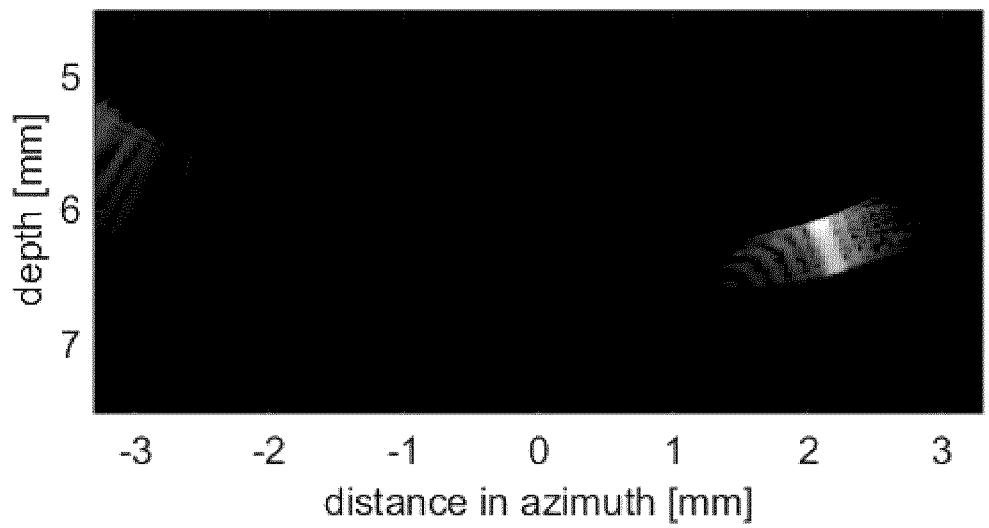
FIGS. 10A and 10B show simulated images of a point scatterer located 20 degrees off axis using a single Fresnel aperture on transmit (FIG. 10A) and then 8 sub-apertures on transmit (FIG. 10B). The images are shown with 30 dB dynamic range.
Figure 10B:
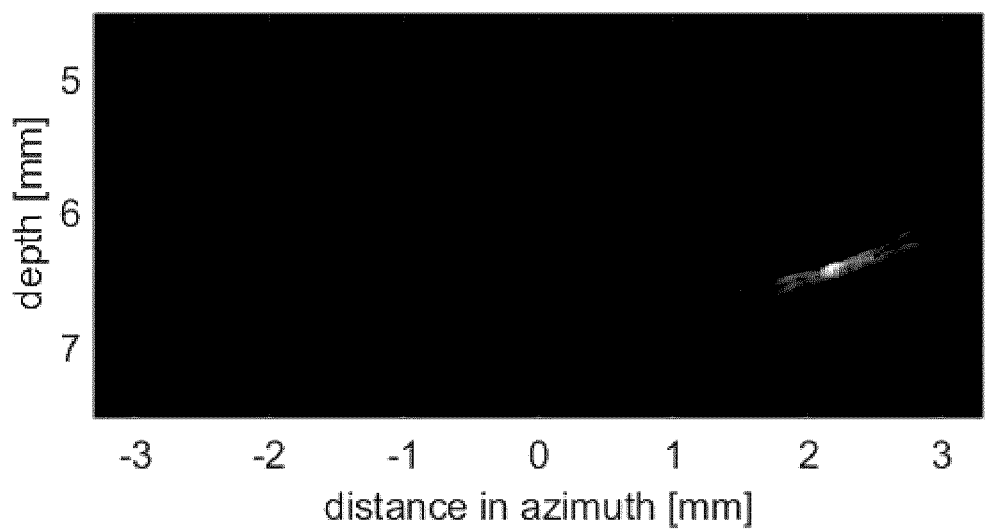

Example 3: Simulated Imaging of Point Scatterer with and with Fresnel Sub-Apertures FIGS. 10A and 10B show simulated images of a point scatterer located 20 degrees off axis using a single Fresnel aperture on transmit (FIG. 10A) and then 8 sub-apertures on transmit (FIG. 10B). The images are shown with 30 dB dynamic range.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

Therefore what is claimed is:

1. An ultrasound imaging system comprising:
an ultrasound transducer comprising:
an array of ultrasound elements, wherein each ultrasound element is capable of acoustic transduction when electrically biased, such that the ultrasound transducer emits ultrasound energy upon the application of voltage pulses thereto when electrically biased;
a first array of first electrodes provided on a first side of said array of ultrasound elements, the first electrodes being spaced along a first direction;
a second array of second electrodes provided on a second side of said array of ultrasound elements, the second electrodes being spaced along a second direction, wherein the first direction and the second direction are configured such that said first array of first electrodes and said second array of second electrodes are arranged in a crossed electrode configuration; and
control and processing hardware operatively coupled to said ultrasound transducer, said control and processing hardware comprising processing electronics configured to perform transmit operations comprising:
providing transmit voltage pulses to said first array of first electrodes and first bias voltages to said second array of second electrodes such that an ultrasound pulse is transmitted to a focal point along a focused line of sight;
wherein the voltage pulses are provided to said first array of first electrodes such that a time delay transmit beamforming aperture is employed for focusing the ultrasound pulse to the focal point in a first plane that includes the first direction and is perpendicular of the emitting surface of the ultrasound transducer; and
wherein the first bias voltages are provided to said second array of second electrodes such that a transmit Fresnel aperture is formed for focusing the ultrasound pulse to the focal point in a second plane that includes the second direction and is perpendicular of the emitting surface of the ultrasound transducer; and
wherein said processing electronics are configured to perform receive operations in a switched configuration with said first array of first electrodes being electrically biased, the receive operations comprising:

applying second bias voltages to said first array of first electrodes and receiving signals with said second array of second electrodes;

wherein the second bias voltages are provided to said first array of first electrodes such that a receive Fresnel aperture is formed for focusing received ultrasound energy from the focal point in the first plane;

wherein the signals obtained from said second array of second electrodes are dynamically beamformed, such that a time delay receive beamforming aperture is employed for focusing the received ultrasound energy in the second plane;

wherein said processing electronics are further configured such that one or both of the transmit Fresnel aperture and the receive Fresnel aperture are sequentially generated as a set of Fresnel sub-apertures, with the signals from the multiple transmit/receive events associated with the set of Fresnel sub-apertures being added together; and wherein said processing electronics are further configured such that:

when the transmit Fresnel aperture is generated as a set of transmit Fresnel sub-apertures, each transmit event that corresponds to a respective transmit Fresnel sub-aperture is delayed by a respective transmit time delay selected to compensate for variations in path lengths between the transmit Fresnel sub-apertures and the focal point; and when the receive Fresnel aperture is generated as a set of receive Fresnel sub-apertures, each signal corresponding to a respective receive Fresnel sub-aperture is delayed by a time delay selected to compensate variations in path lengths between the receive Fresnel sub-apertures and the focal point, prior to adding respective signals from the receive Fresnel sub-apertures together;

wherein said processing electronics are configured to perform transmit operations and receive operations along a plurality of focused lines of sight to generate ultrasound image data for producing an ultrasound image.

2. The ultrasound imaging system according to claim 1 wherein said array of ultrasound elements are defined, within an electrostrictive layer, by said first array of first electrodes and by said second array of second electrodes.

3. The ultrasound imaging system according to claim 1 wherein said array of ultrasound elements comprise capacitive micromachined ultrasound transducer (CMUT) array elements.

4. The ultrasound imaging system according to claim 1 wherein said array of ultrasound elements comprise kerfed electrostrictive array elements.

5. The ultrasound imaging system according to claim 1 wherein the first direction is perpendicular to the second direction.

6. The ultrasound imaging system according to claim 1 wherein the first direction lies within an azimuthal plane, and wherein the second direction lies within an elevation plane.

7. The ultrasound imaging system according to claim 1 wherein said processing electronics are further configured such that both the transmit Fresnel aperture and the receive Fresnel aperture are generated as respective sets of transmit Fresnel sub-apertures and receive Fresnel sub-apertures.

8. The ultrasound imaging system according to claim 7 wherein said processing electronics are further configured such that the set of receive Fresnel sub-apertures are sequentially generated for each transmit Fresnel sub-aperture, such that the total number of transmit/receive events, for a given focused line of sight, is equal to the product of the number of transmit Fresnel sub-apertures and the number of receive Fresnel sub-apertures.

9. The ultrasound imaging system according to claim 7 wherein said processing electronics are further configured such that one or more transmit Fresnel sub-apertures each have a single unique receive Fresnel sub-aperture associated therewith, such that a single transmit/receive event is generated for each one of the one or more transmit Fresnel sub-apertures.

10. The ultrasound imaging system according to claim 7 wherein said processing electronics are configured such that the number of transmit Fresnel sub-apertures equals the number of receive Fresnel sub-apertures.

11. The ultrasound imaging system according to claim 7 wherein said processing electronics are configured such that the number of transmit Fresnel sub-apertures equals the number of receive Fresnel sub-apertures; and wherein said processing electronics are further configured such that a single unique receive Fresnel sub-aperture is generated for each transmit Fresnel sub-aperture.

12. The ultrasound imaging system according to claim 1 wherein said processing electronics are further configured such that the number of Fresnel sub-apertures is dependent on steering angle, such that the number of Fresnel sub-apertures increases with increasing steering angle.

13. The ultrasound imaging system according to claim 12 wherein the number of Fresnel sub-apertures is increased with steering angle at rate suitable for producing a consistent image with respect to resolution.

14. An endoscope comprising the ultrasound imaging system according to claim 1.

15. A method of performing ultrasound imaging using an ultrasound transducer:

the ultrasound transducer comprising:

an array of ultrasound elements, wherein each ultrasound element is capable of acoustic transduction when electrically biased, such that the ultrasound transducer emits ultrasound energy upon the application of voltage pulses thereto when electrically biased;

a first array of first electrodes provided on a first side of said array of ultrasound elements, the first electrodes being spaced along a first direction;

a second array of second electrodes provided on a second side of said array of ultrasound elements, the second electrodes being spaced along a second direction, wherein the first direction and the second direction are configured such that said first array of first electrodes and said second array of second electrodes are arranged in a crossed electrode configuration;

the method comprising:

performing transmit operations by:

providing transmit voltage pulses to said first array of first electrodes and first bias voltages to said second array of second electrodes such that an ultrasound pulse is transmitted to a focal point along a focused line of sight;

wherein the voltage pulses are provided to said first array of first electrodes such that a time delay transmit beamforming aperture is employed for focusing the ultrasound pulse to the focal point in a first plane that includes the first direction and is perpendicular of the emitting surface of the ultrasound transducer; and wherein the first bias voltages are provided to said second array of second electrodes such that a transmit Fresnel aperture is formed for focusing the ultrasound pulse to the focal point in a second plane that includes the second direction and is perpendicular of the emitting surface of the ultrasound transducer; and performing receive operations, in a switched configuration with the first array of first electrodes being electrically biased, by:

applying second bias voltages to said first array of first electrodes and receiving signals with said second array of second electrodes;

wherein the second bias voltages are provided to said first array of first electrodes such that a receive Fresnel aperture is formed for focusing received ultrasound energy from the focal point in the first plane;

wherein the signals obtained from said second array of second electrodes are dynamically beamformed, such that a time delay receive beamforming aperture is employed for focusing the received ultrasound energy in the second plane;

wherein one or both of the transmit Fresnel aperture and the receive Fresnel aperture are sequentially generated as a set of Fresnel sub-apertures, with the signals from the multiple transmit/receive events associated with the set of Fresnel sub-apertures being added together; and wherein one or both of the transmit Fresnel aperture and the receive Fresnel aperture are further configured such that:

when the transmit Fresnel aperture is generated as a set of transmit Fresnel sub-apertures, each transmit event that corresponds to a respective transmit Fresnel sub-aperture is delayed by a respective transmit time delay selected to compensate for variations in path lengths between the transmit Fresnel sub-apertures and the focal point; and when the receive Fresnel aperture is generated as a set of receive Fresnel sub-apertures, each set of signals corresponding to a respective receive Fresnel sub-aperture is delayed by a time delay selected to compensate variations in path lengths between the receive Fresnel sub-apertures and the focal point, prior to adding respective signals from the receive Fresnel sub-apertures;

wherein transmit operations and receive operations are performed along a plurality of focused lines of sight, thereby providing ultrasound image data for generating an ultrasound image.

16. The method according to claim 15 wherein said array of ultrasound elements are defined, within an electrostrictive layer, by said first array of first electrodes and by said second array of second electrodes.

17. The method according to claim 15 wherein said array of ultrasound elements comprise capacitive micromachined ultrasound transducer (CMUT) array elements.

18. The method according to claim 15 wherein said array of ultrasound elements comprise kerfed electrostrictive array elements.

19. The method according to claim 15 wherein the first direction is perpendicular to the second direction.

20. The method according to claim 15 wherein the first direction lies within an azimuthal plane, and wherein the second direction lies within an elevation plane.

21. The method according to claim 15 wherein the transmit Fresnel aperture and the receive Fresnel aperture are generated as respective sets of transmit Fresnel sub-apertures and receive Fresnel sub-apertures.

22. The method according to claim 21 wherein the set of receive sub-apertures are sequentially generated for each transmit Fresnel sub-aperture, such that the total number of transmit/receive events, for a given focused line of sight, is equal to the product of the number of transmit Fresnel sub-apertures and the number of receive Fresnel sub-apertures.

23. The method according to claim 21 wherein one or more transmit Fresnel sub-apertures each have a single unique receive Fresnel sub-aperture associated therewith, such that a single transmit/receive event is generated for each one of the one or more transmit Fresnel sub-apertures.

24. The method according to claim 21 wherein the number of transmit Fresnel sub-apertures equals the number of receive Fresnel sub-apertures.

25. The method according to claim 21 wherein the number of transmit sub-apertures equals the number of receive sub-apertures; and wherein a single unique receive Fresnel sub-aperture is generated for each transmit Fresnel sub-aperture.

26. The method according to claim 15 wherein the number of Fresnel sub-apertures is dependent on steering angle, such that the number of Fresnel sub-apertures increases with increasing steering angle.

27. The method according to claim 26 wherein the number of Fresnel sub-apertures is increased with steering angle at rate suitable for producing a consistent image with respect to resolution.

* * * * *